United States Patent [19]

Yoshida et al.

[11] Patent Number: 5,041,437
[45] Date of Patent: Aug. 20, 1991

[54] PHARMACEUTICAL PREPARATION FOR PERCUTANEOUS ADMINISTRATION CONTAINING BUNAZOSIN OR ITS SALT

[75] Inventors: Mitsuhiro Yoshida; Hiroyuki Fujimori; Hidenori Asakawa, all of Saitama; Masayoshi Kasai, Gifu; Masanori Kayano; Shigemitsu Osawa, both of Saitama, all of Japan

[73] Assignees: Eisai Co., Ltd.; Sansho Co., Ltd., both of Tokyo, Japan

[21] Appl. No.: 428,240

[22] Filed: Oct. 27, 1989

[30] Foreign Application Priority Data

Nov. 11, 1988 [JP] Japan ............................... 63-285428

[51] Int. Cl.$^5$ .................. A61K 31/55; A61K 31/225; A61K 31/23
[52] U.S. Cl. .................................... 514/218; 514/547; 514/552; 514/929
[58] Field of Search ................. 514/218, 929, 547, 552

[56] References Cited

U.S. PATENT DOCUMENTS 4,377,581  3/1983  Hess et al. ............................ 514/260
4,925,837  5/1990  Cavaero et al. ...................... 514/211

FOREIGN PATENT DOCUMENTS

0290089A2  1/1987  European Pat. Off. .
0254978    2/1988  European Pat. Off. .
61-22512  10/1986  Japan .

OTHER PUBLICATIONS

J. Pharm. Pharmacol. vol. 39, 1987, pp. 399-400, A. Kato et al., "Effect of Egg Yolk Lecithin on Transdermal Delivery of Bunazosin Hydrochloride".
Chemical Abstracts, vol. 111, No. 12, No. 102753a (1989).

Primary Examiner—Richard L. Raymond
Assistant Examiner—Gary E. Hollinden
Attorney, Agent, or Firm—Flynn, Thiel, Boutell & Tanis

[57] ABSTRACT

A pharmaceutical composition comprises (a) a pharmacologically effective amount of bunazosin or a pharmacologically acceptable salt thereof and (b) a monoglyceride of a fatty acid having 8 to 12 carbon atoms and/or a lactic acid ester of an aliphatic alcohol having 12 to 18 carbon atoms and is improved in percutaneous administration.

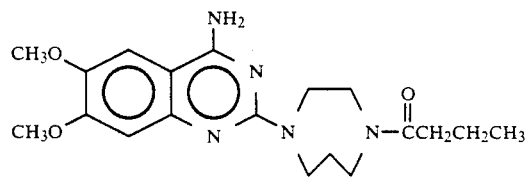

10 Claims, 2 Drawing Sheets

SKIN PENETRATION OF BUNAZOCINE HYDROCHLORIDE

SKIN PENETRATION OF BUNAZOCINE HYDROCHLORIDE

PHARMACEUTICAL PREPARATION FOR PERCUTANEOUS ADMINISTRATION CONTAINING BUNAZOSIN OR ITS SALT

The present invention relates on a pharmaceutical preparation for percutaneous administration containing bunazosin or its salt, and more particularly on a pharmaceutical preparation for percutaneous administration containing bunazosin or its salt which is excellent in the permeation into the skin.

PRIOR ART

Bunazosin or its salt is a 6,7-dimethoxyquinazoline derivative which exhibits a hypotensive activity through blocking of a sympathetic α-receptor and known as a therapeutic agent for essential hypertension and renal hypertension. At the present time, bunazosin hydrochloride preparations are limited to oral administration.

It is known that percutaneous administration is more advantageous than oral administration in that the drug is more effectively utilized in the body because of the avoidance of a first-pass effect in the liver and that a persistent effect can be obtained. In particular, in the case of the above-described drug, persistence of the drug effect is desired.

For this purpose, efficient percutaneous absorption of the drug should be first attained. The present inventors have made extensive and intensive studies with a view to enhancing the percutaneous absorption of bunazosin or its salt and examined a possibility of obtaining a pharmaceutical preparation for percutaneous absorption through which the persistence of the hypotensive activity can be expected.

In order to prepare a pharmaceutical preparation for percutaneous absorption through the use of bunazosin or its salt, it is necessary to use a vehicle which can dissolve bunazosin or its salt to a suitable extent and improve the permeation of bunazosin or its salt into the skin. The present inventors have made extensive and intensive studies with a view to finding these vehicles.

The present inventors have found through their studies that a monoglyceride of a fatty acid having 8 to 12 carbon atoms or/and an ester of lactic acid with an aliphatic alcohol having 12 to 18 carbon atoms can dissolve bunazosin or its salt to a more suitable extent than that in the case of conventional vehicles and remarkably improve the permeation of bunazosin or its salt into the skin, which has led to the completion of the present invention.

Bunazosin hydrochloride is a compound represented by the following structural formula:

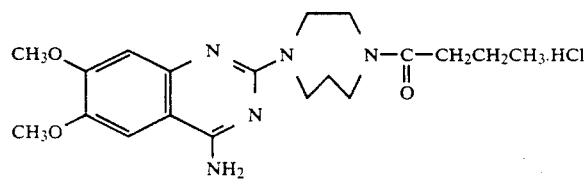

A pharmaceutical composition comprises (a) a pharmacologically effective amount of bunazosin or a pharmacologically acceptable salt thereof and (b) a monoglyceride of a fatty acid having 8 to 12 carbon atoms and/or a lactic acid ester of an aliphatic alcohol having 12 to 18 carbon atoms and is improved in percutaneous administration.

It is preferred that a weight ratio of (b) to (a) ranges from 0.1 to 200.

Accordingly, the present invention provides a pharmaceutical preparation for percutaneous administration containing bunazosin or its salt which comprises bunazosin or its salt and a monoglyceride of a fatty acid having 8 to 12 carbon atoms or/and an ester of lactic acid with an alphatic alcohol having 12 to 18 carbon atoms incorporated therein.

Examples of the monoglyceride of a fatty acid having 8 to 12 carbon atoms include glyceryl monocaprylate, glyceryl monocaproate, and glyceryl monolaurate, among which glyceryl monocaprylate is particularly preferred.

Examples of the ester of lactic acid with an aliphatic alcohol having 12 to 18 carbon atoms include myristyl lactate, cetyl lactate, and lauryl lactate.

It is suitable to incorporate the monoglyceride of a fatty acid having 8 to 12 carbon atoms or/and the ester of lactic acid with an aliphatic alcohol having 12 to 18 carbon atoms in a combined amount of from 0.1 to 200 parts by weight based on the amount of bunazosin or its salt. It is preferred that bunazosin or its salt be incorporated in the pharmaceutical preparation in an amount of 0.1 to 20% by weight and the monoglyceride of a fatty acid having 8 to 12 carbon atoms and/or the ester of lactic acid with an aliphatic alcohol having 12 to 18 carbon atoms be incorporated in the pharmaceutical preparation in a total amount of 1 to 20% by weight.

It is possible to further improve the permeation of bunazosin or its salt by an increase in the pH value of the pharmaceutical preparation of the present invention wherein the monoglyceride of a fatty acid having 8 to 12 carbon atoms or/and the ester of lactic acid with an aliphatic alcohol having 12 to 18 carbon atoms are incorporated.

There is no particular limitation on the form of the pharmaceutical preparation of the present invention, and the pharmaceutical preparation may be in the form of any of ointments, creams, patches, lotions, etc.

All of the vehicle ingredients commonly used as pharmaceutical preparations for percutaneous administration may be used as ingredients in addition to the monoglyceride of a fatty acid having 8 to 12 carbon atoms or/and the ester of lactic acid with an aliphatic alcohol having 12 to 18 carbon atoms contained in the pharmaceutical preparation of the present invention, and any of oleaginous base ingredients and aqueous base ingredients may be used. Examples of the oleaginous base ingredients include white petrolatum, purified lanolin, squalane, silicone, liquid paraffin, vegetable oils, and waxes. Examples of the aqueous base ingredients include water, lower alcohols, polyhydric alcohols, and water-soluble polymers. Examples of the base ingredient, e.g., polymer compositions, which are commonly used for the patch include those having tackiness, such as natural rubbers, synthetic rubbers, styrene-isoprene-styrene block copolymers (SIS), polyacrylic ester resins and polyisobutylene resins; soft polyamide resins; polyvinyl alcohol; and polyacrylic resin.

Besides the above-described components, the pharmaceutical preparation of the present invention may contain optional additives used in known pharmaceutical preparations for percutaneous administration, such as surfactants, stabilizers, preservatives, and antiseptics.

The pharmaceutical preparation of the present invention has the following advantages.

(1) Its availability is high because it is free from a first-pass effect in the liver.

(2) It brings no gastro-intestinal disturbances.

(3) Its action is persistent.

(4) Its administration can be immediately interrupted when adverse reactions (e.g., hypersensitive symptom such as eruption) were observed, so that high safety can be attained.

(5) Since an increase of the drug concentration in blood is slower in percutaneous administration than that of oral administration, it is possible to prevent vertigo and lightheadedness attributable to rapid blood pressure decrease.

EXAMPLES

The present invention will now be described in more detail by way of Experimental Examples which demonstrate the effect of the monoglyceride of a fatty acid having 8 to 12 carbon atoms or/and the ester of lactic acid with an aliphatic alcohol having 12 to 18 carbon atoms on the permeation of bunazosin or its salt into the skin. The Examples of the present invention should not be construed as limiting the scope of the present invention.

EXPERIMENTAL EXAMPLE 1

The following various test samples were prepared to conduct experiments on skin permeation in vitro.

Figure 1:
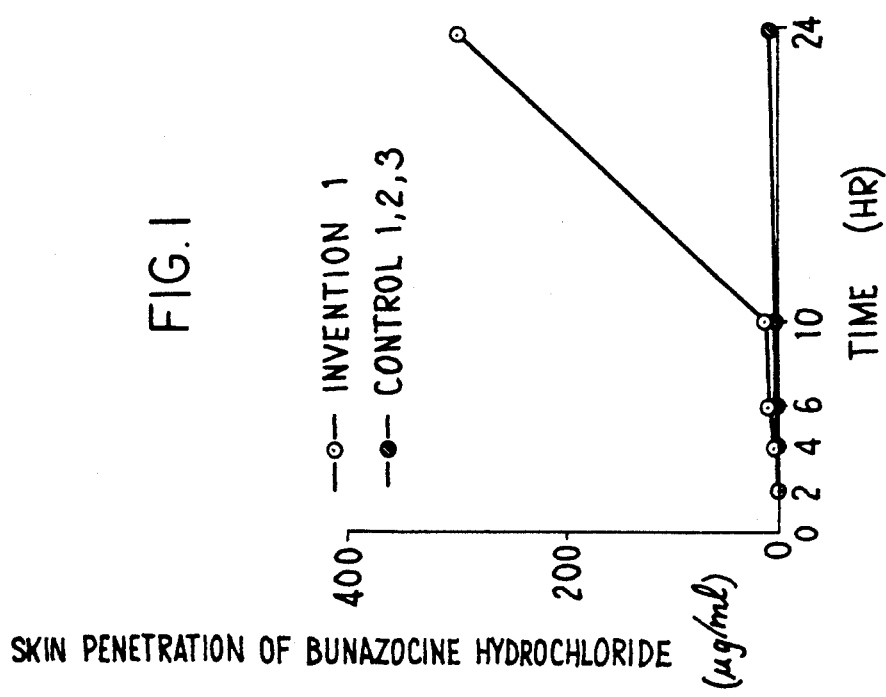

The results are shown in FIG. 1.

PREPARATION OF TEST SAMPLES

Sample 1 of the present invention

A propylene glycol solution containing 5% by weight of glycerin mono/dicaprylate (Homotex PT ® which contains glycerin monocaprylate and glycerin dicaprylate in a weight ratio of 1:1; a product of Kao Corp.) was used as a base, and bunazosin hydrochloride was suspended in the base to prepare a sample (containing 200 mg of bunazosin hydrochloride in 2 g of the sample).

COMPARATIVE SAMPLE 1

Propylene glycol was used as a base, and bunazosin hydrochloride was suspended in the base (containing 200 mg of bunazosin hydrochloride in 2 g of the sample).

COMPARATIVE SAMPLE 2

1,3-Butylene glycol was used as a base, and bunazosin hydrochloride was suspended in the base to prepare a sample (containing 200 mg of bunazosin hydrochloride in 2 g of the sample).

COMPARATIVE SAMPLE 3

Dipropylene glycol was used as a base, and bunazosin hydrochloride was suspended in the base to prepare a sample (containing 200 mg of bunazosin hydrochloride in 2 g of the sample).

METHOD OF EXPERIMENT ON SKIN PENETRATION IN VITRO

Abdominal hair of a male Wistar rat weighing about 230 g (8- to 9-week old) was removed under anesthesia. After 24 hr, the rat was similarly anesthetized to confirm that the skin was free from a wound. Then, the skin was cleanly wiped with 70% ethanol, followed by ablation of the entire skin of the abdomen.

The ablated skin was fixed to the lid of a horizontal membrane type in-vitro diffusion cell having a permeation area of 7.54 cm$^2$ in such a manner that the skin side served as a donor surface. 50 ml of a phosphate buffer having a pH value of 7.4 was used as a receptor solution. 2 g of the sample solution was dropped and applied to the donor side. The lid was carefully fixed to the receptor so that no bubbles remained on the derims side, followed by incubation in an incubator at 32° C. The receptor solution was stirred with a stirrer and sampled in an amount of 0.5 ml at predetermined time intervals to quantitatively determine bunazosin hydrochloride. The quantitative determination was conducted by high-performance liquid chromatography.

As can be seen from the results shown in FIG. 1, the 24 hr-cumulative skin penetration of bunazosin hydrochloride when a propylene glycol solution containing 5% by weight of glycerin mono/dicaprylate was used as the basic formulation was remarkably excellent and as high as about 40 times compared with that when propylene glycol, 1,3-butylene glycol, or dipropylene glycol was used as the basic ingredient.

EXPERIMENTAL EXAMPLE 2

The following test samples were prepared to conduct experiments on skin penetration in vitro in the same manner as that of Experimental Example 1.

Figure 2:
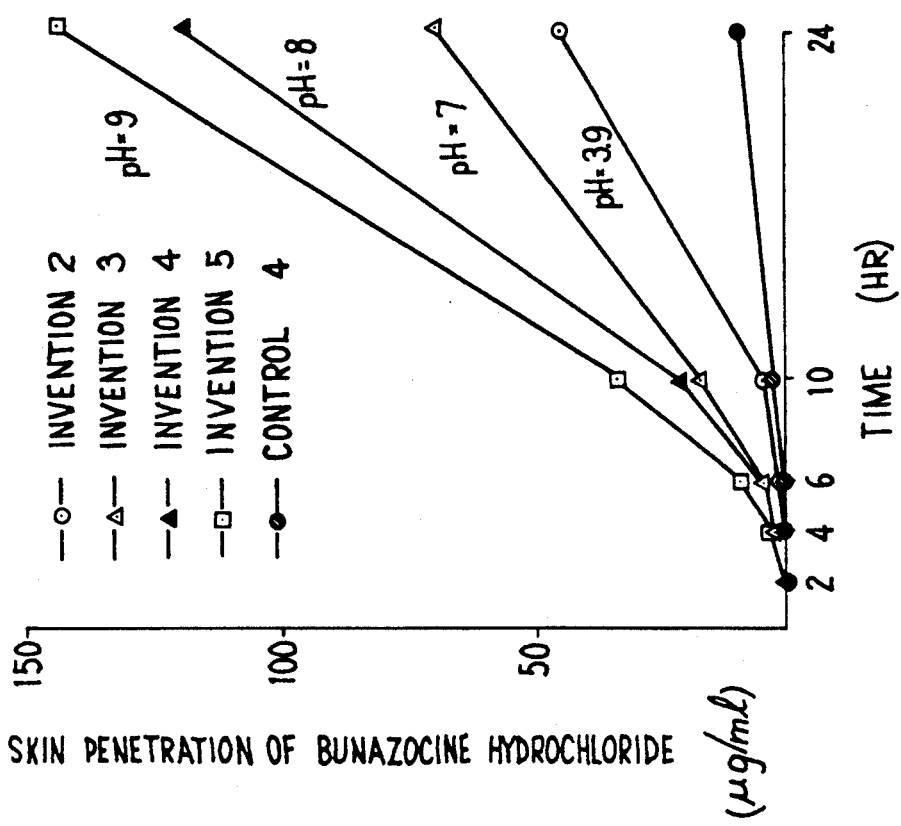
FIGS. 1 to 4 are graphs, respectively showing the results of experiments on skin permeability with samples described in Experimental Examples 1 to 4.

The results are shown in FIG. 2.

PREPARATION OF TEST SAMPLES

Sample 2 of the present invention

A propylene glycol solution containing 5% by weight of cetyl lactate was used as a vehicle, and bunazosin hydrochloride was suspended in the vehicle to prepare a sample (containing 200 mg of bunazosin hydrochloride in 2 g of the sample; pH value: 3.9).

Sample 3 of the present invention

A propylene glycol solution containing 5% by weight of cetyl lactate was used as a base, and bunazosin hydrochloride was suspended in the base to prepare a sample (containing 200 mg of bunazosin hydrochloride in 2 g of the sample).

The pH of the sample was adjusted to 7 with a 1N aqueous NaOH solution.

Sample 4 of the present invention

A propylene glycol solution containing 5% by weight of cetyl lactate was used as a base, and bunazosin hydrochloride was suspended in the base to prepare a sample (containing 200 mg of bunazosin hydrochloride in 2 g of the sample).

The pH of the sample was adjusted to 8 with a 1N aqueous NaOH solution.

Sample 5 of the present invention

A propylene glycol solution containing 5% by weight of cetyl lactate was used as a base, and bunazosin hydrochloride was suspended in the base to prepare a sample (containing 200 mg of bunazosin hydrochloride in 2 g of the sample).

The pH of the sample was adjusted to 9 with a 1N aqueous NaOH solution.

COMPARATIVE SAMPLE 4

A propylene glycol solution was used as a base, and bunazosin hydrochloride wa suspended in the base to prepare a sample (containing 200 mg of bunazosin hydrochloride in 2 g of the sample; pH value: 3.9).

As can be seen from the results shown in FIG. 2, the skin penetration of bunazosin hydrochloride, when a solution containing cetyl lactate was used as the base ingredient, was remarkably superior to that when only propylene glycol was used as the base ingredient.

Further, in FIG. 2, the skin penetration was improved with an increase in the pH value of the sample of the present invention.

EXPERIMENTAL EXAMPLE 3

The following various test samples were prepared to conduct experiments on skin penetration in vitro in the same manner as that of Experimental Example 1.

Figure 3:
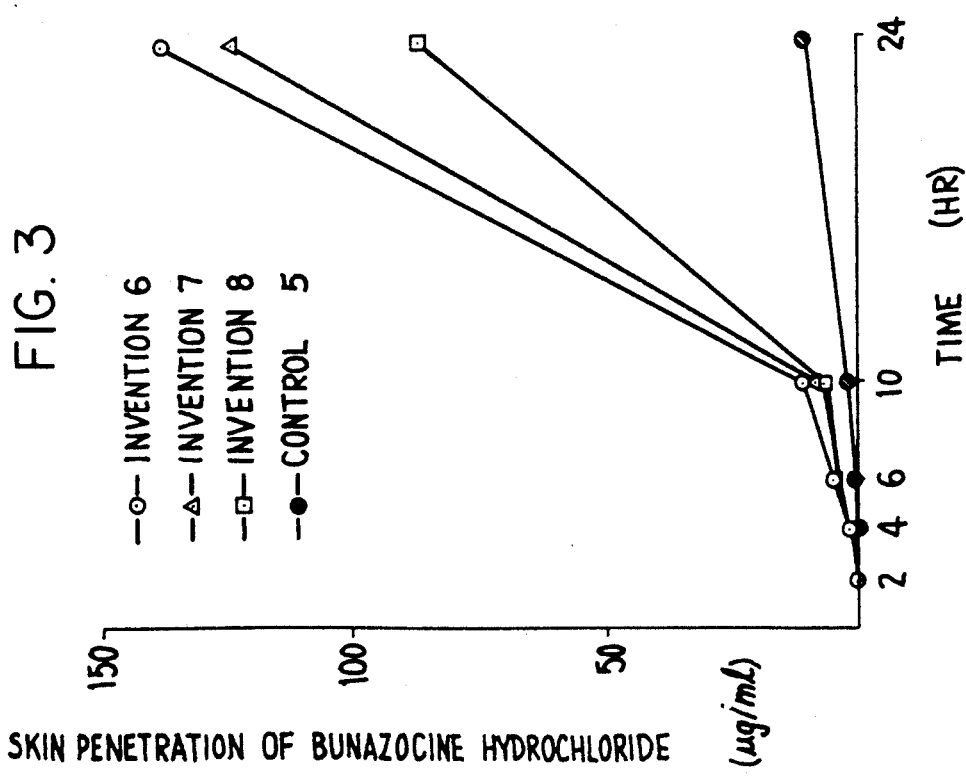

The results are shown in FIG. 3.

PREPARATION OF TEST SAMPLES

Sample 6 of the present invention

A propylene glycol dicaprylate solution containing 5% by weight of glycerin monocaprylate was used as a base, and bunazosin hydrochloride was suspended in the base to prepare a sample (containing 200 mg of bunazosin hydrochloride in 2 g of the sample).

Sample 7 of the present invention

A propylene glycol dicaprylate solution containing 5% by weight of glycerin monocaprate was used as a base, and bunazosin hydrochloride was suspended in the base to prepare a sample (containing 200 mg of bunazosin hydrochloride in 2 g of the sample).

Sample 8 of the present invention

A propylene glycol dicaprylate solution containing 5% by weight of glycerin monolaurate was used as a base, and bunazosin hydrochloride was suspended in the base to prepare a sample (containing 200 mg of bunazosin hydrochloride in 2 g of the sample).

COMPARATIVE SAMPLE 5

A propylene glycol dicaprylate was used as a base, and bunazosin hydrochloride was suspended in the base to prepare a sample (containing 200 mg of bunazosin hydrochloride in 2 g of the sample).

As can be seen from the results shown in FIG. 3, the skin penetration of bunazosin hydrochloride when a propylene glycol dicaprylate solution containing a monoglyceride of an aliphatic acid having 8 to 12 carbon atoms was used as the base ingredient was remarkably superior to that when only propylene glycol dicaprylate was used as the base ingredient.

EXPERIMENTAL EXAMPLE 4

The following various test samples were prepared to conduct experiments on skin penetration in vitro in the same manner as that of Experimental Example 1.

Figure 4:
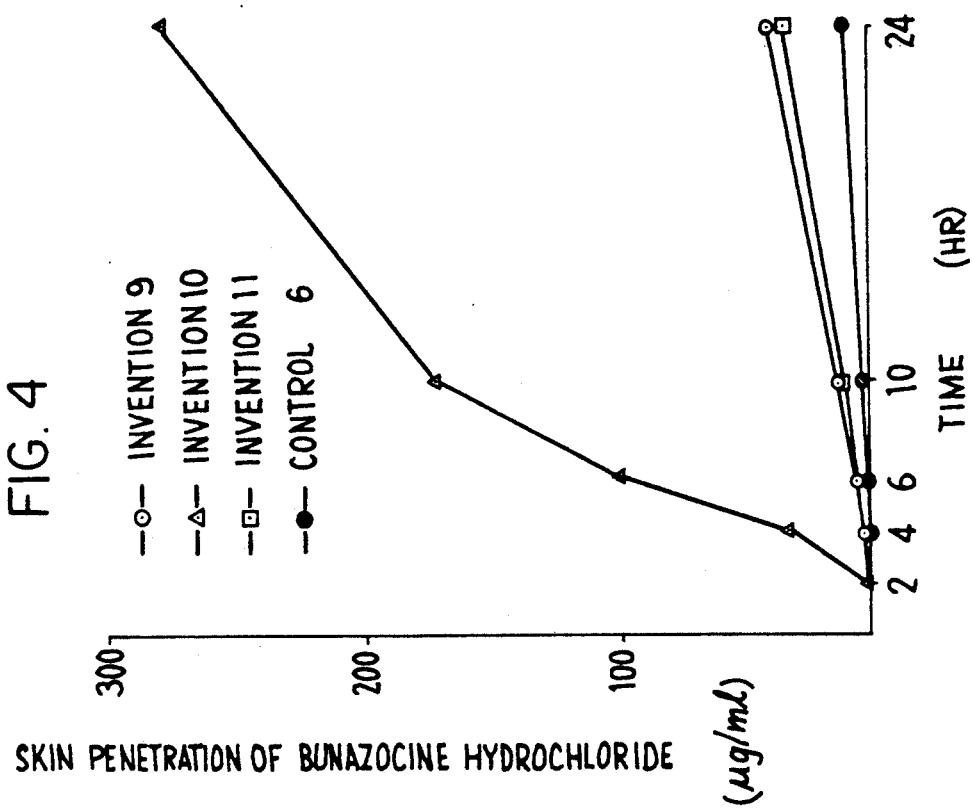

The results are shown in FIG. 4.

PREPARATION OF TEST SAMPLES

Sample 9 of the present invention

A propylene glycol solution containing 5% by weight of cetyl lactate was used as a base, and bunazosin hydrochloride was suspended in the base to prepare a sample (containing 200 mg of bunazosin hydrochloride in 2 g of the sample).

Sample 10 of the present invention

A propylene glycol solution containing 5% by weight of myristyl lactate was used as a base, and bunazosin hydrochloride was suspended in the base to prepare a sample (containing 200 mg of bunazosin hydrochloride in 2 g of the sample).

Sample 11 of the present invention

A propylene glycol solution containing 5% by weight of lauryl lactate was used as a base, and bunazosin hydrochloride was suspended in the base to prepare a sample (containing 200 mg of bunazosin hydrochloride in 2 g of the sample).

COMPARATIVE SAMPLE 6

Propylene glycol was used as a base, and bunazosin hydrochloride was suspended in the base to prepare a sample (containing 200 mg of bunazosin hydrochloride in 2 g of the sample).

As can be seen from the results shown in FIG. 4, the skin penetration of bunazosin hydrochloride when a propylene glycol dicaprylate solution containing an ester of lactic acid with an aliphatic alcohol having 12 to 18 carbon atoms was used as the base ingredient was remarkably superior to that when only propylene glycol was used as the base ingredient.

EXAMPLE 1 (OLEAGINOUS OINTMENT)

Glycerin mono/dicaprylate (Homotex PT ®) was heated at 60° C. and bunazosin hydrochloride was added thereto, followed by stirring to prepare a homogeneous mixture. Separately, sorbitan trioleate and white petrolatum were heated to 60° C. to homogeneously mix them with each other. The above homogeneous mixture prepared by stirring the glycerin mono/dicaprylate and bunazosin hydrochloride was added thereto. All of them were stirred to homogeneously mix them with each other. The mixture was allowed to cool at room temperature to prepare an oleaginous ointment having the following composition:

| | |
|---|---|
| bunazosin hydrochloride | 1.5% by weight |
| glycerin mono/dicaprylate (Homotex PT ®) | 5% by weight |
| sorbitan trioleate | 3% by weight |
| white petrolatum | 90.5% by weight |

EXAMPLE 2 (HYDROPHILIC OINTMENT)

Glycerin monocaprylate, polyoxyethylene(20) sorbitan monooleate, macrogol ointment listed in the Pharmacopoeia of Japan, and a preservative were heated to 60° C. and homogeneously mixed with each other. A finely divided powder of bunazosin hydrochloride was added thereto. They were sufficiently mixed with each other while cooling, thereby preparing a hydrophilic ointment having the following composition:

| | |
|---|---|
| bunazosin hydrochloride | 2% by weight |
| glycerin monocaprylate | 3% by weight |

| | |
|---|---|
| polyoxyethylene(20) sorbitan monooleate | 2% by weight |
| macrogol ointment listed in the Pharmacopoeia of Japan | 92.9% by weight |
| preservative | 0.1% by weight |

EXAMPLE 3 (O/W TYPE CREAM)

Squalane, isopropyl myristate, stearic acid, glycerin monostearate, sorbitan monopalmitate, polyoxyethylene(20) sorbitan monostearate, and glycerin monocaprylate were heated together to 70° C. for homogeneous dissolution. Bunazosin hydrochloride was added to the resultant solution and stirred to prepare a homogeneous mixture. Propylene glycol, a preservative, and purified water heated to 60° C. were gradually added thereto, and the mixture was allowed to cool to 30° C. while stirring, thereby preparing an O/W type cream having the following composition:

| | |
|---|---|
| bunazosin hydrochloride | 2% by weight |
| squalane | 8% by weight |
| isopropyl myristate | 4% by weight |
| stearic acid | 4% by weight |
| glycerin monostearate | 4% by weight |
| sorbitan monopalmitate | 1.5% by weight |
| polyoxyethylene(20) sorbitan monostearate | 1.5% by weight |
| glycerin monocaprylate | 5% by weight |
| preservative | 0.1% by weight |
| purified water | 64.9% by weight |

EXAMPLE 4 (OLEAGINOUS OINTMENT)

Glycerin monolaurate and glycerin monocaprylate were heated to 55° C., and bunazosin hydrochloride was added thereto to prepare a homogeneous mixture. This homogeneous mixture was added to a mixture of octyldodecyl myristate, sorbitan sesquioleate, purified lanolin, propylene glycol monostearate, and white petrolatum heated to 70° C. to prepare a homogeneous mixture and then allowed to cool while stirring, thereby preparing an oleaginous ointment having the following composition:

| | |
|---|---|
| bunazosin hydrochloride | 1% by weight |
| glycerin monolaurate | 3% by weight |
| glycerin monocaprylate | 3% by weight |
| octyldodecyl myristate | 10% by weight |
| sorbitan sesquioleate | 5% by weight |
| purified lanolin | 10% by weight |
| propylene glycol monostearate | 2% by weight |
| white petrolatum | 66% by weight |

EXAMPLE 5 (OLEAGINOUS OINTMENT)

Propylene glycol was heated to 60° C., and bunazosin hydrochloride was added and dissolved therein. A mixture of cetyl lactate with Plastibase (trademark of a product of Squibb Japan Inc.; a mixture of 95% by weight of liquid paraffin with 5% by weight of polyethylene having a molecular weight of 10,000 to 30,000) prepared by heating them together to 60° C. was added to the resultant solution. The mixture was allowed to cool at room temperature while stirring, thereby preparing an oleaginous ointment having the following composition:

| | |
|---|---|
| bunazosin hydrochloride | 5% by weight |
| cetyl lactate | 10% by weight |
| propylene glycol | 15% by weight |
| Plastibase | 70% by weight |

EXAMPLE 6 (OLEAGINOUS OINTMENT)

Propylene glycol was heated to 70° C., and bunazosin hydrochloride, Homotex PT ®, cetyl lactate, cetostearyl alcohol, stearic acid, and propylene glycol monostearate were added and dissolved therein. The resultant solution was added to Plastibase heated to 70° C., and kneaded and mixed. The mixture was allowed to cool while stirring to prepare an ointment having the following composition:

| | |
|---|---|
| bunazosin hydrochloide | 10% by weight |
| glycerin mono/dicaprylate (Homotex PT ®) | 5% by weight |
| cetyl lactate | 10% by weight |
| cetostearyl alcohol | 3% by weight |
| stearic acid | 3% by weight |
| propylene glycol monostearate | 8% by weight |
| propylene glycol | 25% by weight |
| Plastibase | 36% by weight |

EXAMPLE 7 (PATCH)

A solution prepared by heating a mixture of SIS rubber, Arkon P-100 ® (alicyclic petroleum resin) and liquid paraffin to 130° C. was mixed with a solution prepared by heating bunazosin hydrochloride, Homotex PT ®, cetyl lactate, glycerin monoolate, and dibutylhydroxytoluene together to 70° C. The mixture was extended on a suitable support to prepare a patch having the following composition:

| | |
|---|---|
| SIS rubber | 35% by weight |
| Arkon P-100 ® | 24% by weight |
| liquid paraffin | 18% by weight |
| bunazosin hydrochloride | 2% by weight |
| Homotex PT ® | 10% by weight |
| cetyl lactate | 5% by weight |
| glycerin monoolate | 5% by weight |
| dibutylhydroxytoluene | 1% by weight |

EXAMPLE 8 (GEL-FORM OINTMENT)

1.5 parts by weight of Carbopol 940 ® (carboxyvinyl polymer; a product of Goodrich) was suspended in 15 parts by weight of propylene glycol containing ethylparaben and propylparaben each dissolved therein. A suitable amount of purified water was added to the suspension while stirring to prepare a homogeneous slurry. Separately, bunazosin hydrochloride, cetyl lactate, and Homotex PT ® were added to 15 parts by weight of propylene glycol, and the mixture was heated to prepare a solution. The slurry prepared above was gradually added to this solution to prepare a homogeneous gel-form ointment having the following composition:

| | |
|---|---|
| bunazosin hydrochloride | 5% by weight |
| cetyl lactate | 5% by weight |
| Homotex PT ® | 5% by weight |
| Carbopol 940 ® | 1.5% by weight |
| propylene glycol | 30% by weight |

| | |
|---|---|
| ethylparaben | 0.05% by weight |
| propylparaben | 0.15% by weight |
| purified water | a suitable amount |
| in total | 100.0 |

What is claimed is:

1. A pharmaceutical composition which comprises (a) a therapeutically effective amount of bunazosin or a pharmacologically acceptable salt thereof and (b) a lactic acid ester of an aliphatic alcohol having 12 to 18 carbon atoms.

2. The composition as claimed in claim 1, in which a weight ratio of (b) to (a) ranges from 0.1 to 200.

3. The composition as claimed in claim 1, which comprises 0.1 to 20 percent by weight of (a) and 1 to 20 percent by weight of (b).

4. The composition as claimed in claim 1, in which (b) is a lactic acid ester of an aliphatic alcohol having 12 to 18 carbon atoms.

5. The composition as claimed in claim 4, in which the lactic acid ester is selected from the group consisting of myristyl lactate, cetyl lactate and lauryl lactate.

6. The composition as claimed in claim 1 additionally comprising a monoglyceride of a fatty acid having 8 to 12 carbon atoms.

7. A pharmaceutical composition which consists essentially of (a) a therapeutically effective amount of bunazosin or a pharmacologically acceptable salt thereof and (b) at least one of the group of a monoglyceride of a fatty acid having 8 to 12 carbon atoms and a lactic acid ester of an aliphatic alcohol having 12 to 18 carbon atoms.

8. The composition as claimed in claim 7, in which (b) is a monoglyceride of a fatty acid having 8 to 12 carbon atoms and a lactic acid ester of an aliphatic alcohol having 12 to 18 carbon atoms.

9. The composition as claimed in claim 7, in which (b) is a monoglyceride of a fatty acid having 8 to 12 carbon atoms.

10. The composition as claimed in claim 7, in which (b) is a lactic acid ester of an aliphatic alcohol having 12 to 18 carbon atoms.

* * * * *

UNITED STATES PATENT AND TRADEMARK OFFICE
CERTIFICATE OF CORRECTION

PATENT NO. : 5 041 437
DATED : August 20, 1991
INVENTOR(S) : Mitsuhiro YOSHIDA et al It is certified that error appears in the above-identified patent and that said Letters Patent is hereby corrected as shown below:

On the title page at item [57]; delete the formula following the ABSTRACT.

Signed and Sealed this

Ninth Day of March, 1993

*Attest:*

STEPHEN G. KUNIN

*Attesting Officer*     *Acting Commissioner of Patents and Trademarks*